(12) United States Patent
Zhao et al.

(10) Patent No.: US 7,098,292 B2
(45) Date of Patent: Aug. 29, 2006

(54) MOLDED OR EXTRUDED ARTICLES COMPRISING POLYHYDROXYALKANOATE COPOLYMER AND AN ENVIRONMENTALLY DEGRADABLE THERMOPLASTIC POLYMER

(75) Inventors: Jean Jianqun Zhao, Cincinnati, OH (US); Isao Noda, Fairfield, OH (US); Gary Wayne Gilbertson, Liberty Township, OH (US); Drew Clifton McAvoy, Cincinnati, OH (US); Brian Francis Gray, Cincinnati, OH (US); David Harry Melik, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 466 days.

(21) Appl. No.: 10/431,796

(22) Filed: May 8, 2003

(65) Prior Publication Data

US 2004/0225269 A1 Nov. 11, 2004

(51) Int. Cl.
*C08G 63/02* (2006.01)
(52) U.S. Cl. .................. 528/272; 264/176.1; 264/219; 435/135; 528/271; 604/11; 604/14
(58) Field of Classification Search ............ 264/176.1, 264/219; 435/135; 528/271, 272; 604/11, 604/14
See application file for complete search history.

(56) References Cited

U.S. PATENT DOCUMENTS

| | | |
|---|---|---|
| 4,900,299 A | 2/1990 | Webb |
| 5,229,279 A | 7/1993 | Peoples et al. |
| 5,292,860 A | 3/1994 | Shiotani et al. |
| 5,462,983 A | 10/1995 | Bloembergen et al. |
| 5,464,689 A | 11/1995 | Matsumura et al. |
| 5,489,470 A | 2/1996 | Noda |
| 5,498,692 A | 3/1996 | Noda |
| 5,502,116 A | 3/1996 | Noda |
| 5,534,432 A | 7/1996 | Peoples et al. |
| 5,536,564 A | 7/1996 | Noda |
| 5,602,227 A | 2/1997 | Noda |
| 5,618,855 A | 4/1997 | Noda |
| 5,653,930 A | 8/1997 | Noda et al. |
| 5,685,756 A | 11/1997 | Noda |
| 5,693,389 A | 12/1997 | Liggat |
| 5,738,646 A | 4/1998 | Fox et al. |
| 5,747,584 A | 5/1998 | Noda |
| 5,780,368 A | 7/1998 | Noda |
| 5,800,758 A | 9/1998 | Topolkaraev et al. |
| 5,821,299 A | 10/1998 | Noda et al. |
| 5,844,023 A | 12/1998 | Tomka |
| 5,849,854 A | 12/1998 | Noda |
| 5,874,486 A | 2/1999 | Bastioli et al. |
| 5,910,520 A | 6/1999 | Dabi et al. |
| 5,914,184 A | 6/1999 | Morman |
| 5,932,497 A | 8/1999 | Morman et al. |
| 5,942,597 A | 8/1999 | Noda et al. |
| 5,955,187 A | 9/1999 | McCormack et al. |
| 5,968,643 A | 10/1999 | Topolkaraev et al. |
| 5,973,100 A | 10/1999 | Asrar et al. |
| 5,990,271 A | 11/1999 | Noda |
| 6,002,064 A | 12/1999 | Kobylivker et al. |
| 6,013,590 A | 1/2000 | Noda |
| 6,015,764 A | 1/2000 | McCormack et al. |
| RE36,548 E | 2/2000 | Noda |
| 6,027,787 A | 2/2000 | Noda |
| 6,033,747 A | 3/2000 | Shiotani |
| 6,045,908 A | 4/2000 | Nakajima et al. |
| 6,077,931 A | 6/2000 | Noda |
| 6,096,809 A | 8/2000 | Lorcks et al. |
| 6,117,925 A | 9/2000 | Tomka |
| 6,143,947 A | 11/2000 | Noda |
| 6,160,199 A | 12/2000 | Noda |
| 6,174,990 B1 | 1/2001 | Noda |
| 6,191,203 B1 | 2/2001 | Asrar et al. |
| 6,225,438 B1 | 5/2001 | Green |
| 2002/0042599 A1 | 4/2002 | Zhao et al. |
| 2002/0143116 A1 | 10/2002 | Noda et al. |
| 2002/0143136 A1 | 10/2002 | Noda et al. |
| 2002/0188041 A1 | 12/2002 | Bond et al. |
| 2003/0036721 A1 | 2/2003 | Zhao et al. |
| 2003/0108701 A1 | 6/2003 | Bond et al. |
| 2003/0191210 A1* | 10/2003 | Autran ........................ 523/105 |
| 2004/0059047 A1 | 3/2004 | Autran et al. |

FOREIGN PATENT DOCUMENTS

| | | |
|---|---|---|
| EP | 0753539 | 1/1997 |
| EP | 0993832 | 4/2000 |
| JP | 10147653 | 6/1998 |

(Continued)

OTHER PUBLICATIONS

Gagnon, K.D.; Lenz, R.W.; Farris, R.J.; Fuller, R.C.; *Crystallization Behavior and Its Influence on the Mechanical Properties of a Thermoplastic Elastomer Produced by Pseudomonas oleovorans*, Macromolecules, American Chemical Society, 25:pp. 3723-3728 (1992).

(Continued)

*Primary Examiner*—Terressa Boykin
(74) *Attorney, Agent, or Firm*—Julie A. McConihay; Leonard W. Lewis

(57) ABSTRACT

Environmentally degradable molded or extruded articles comprising a blend of polyhydroxyalkanoate copolymer and an environmentally degradable thermoplastic polymer or copolymer are disclosed. Such compositions provide annealing cycle times to form molded or extruded articles that are less than annealing cycle times to form a molded or extruded article lacking the environmentally degradable thermoplastic polymer or copolymer.

27 Claims, No Drawings

FOREIGN PATENT DOCUMENTS

| | | |
|---|---|---|
| JP | 11269754 | 10/1999 |
| WO | WO 95/20615 | 8/1995 |
| WO | WO 96/08535 | 3/1996 |
| WO | WO 98/28134 | 7/1998 |
| WO | WO 98/28135 | 7/1998 |
| WO | WO 98/29246 | 7/1998 |
| WO | WO 98/29247 | 7/1998 |
| WO | WO 98/29481 | 7/1998 |
| WO | WO 98/44025 | 10/1998 |
| WO | WO 98/51474 | 11/1998 |
| WO | WO 99/05209 | 2/1999 |
| WO | WO 99/12734 | 3/1999 |
| WO | WO 99/14047 | 3/1999 |
| WO | WO 99/14262 | 3/1999 |
| WO | WO 99/14263 | 3/1999 |
| WO | WO 99/23139 | 5/1999 |
| WO | WO 99/23140 | 5/1999 |
| WO | WO 99/32272 | 7/1999 |
| WO | WO 99/67095 | 12/1999 |
| WO | WO 01/30893 A1 | 5/2001 |
| WO | WO 02/13877 A2 | 2/2002 |
| WO | WO 02/46277 | 6/2002 |
| WO | WO 02/74352 | 9/2002 |
| WO | WO 02/85983 | 10/2002 |

OTHER PUBLICATIONS

Fukui, T and Doi, Y.; *Efficient Production of Polyhydroxyalkanoates From Plant Oils by Alcaligenes Eutrophus and its Recombinant Strain*, Appl Microbiol Biotechnol, 49:pp. 333-336 (1998), Springer-Verlag.

Kichise, Tomoyasu; Fukui, Toshiaki; Yoshida, Yasuhiko; Doi, Yoshiharu; *Biosynthesis of Polyhydroxyalkanoates (PHA) by Recombinant Ralstonia Eutropha and Effects of PHA Synthase Activity on in Vivo PHA Biosynthesis*, International Journal of Biological Macromolecules, 25:pp. 69-77 (1999), Elsevier Science.

Buchanan, Charles M., et al., Cellulose Acetate Butyrate and Poly(hydroxybutyrate-*co*-valerate) Copolymer Blends, *Macromolecules*, vol. 25, No. 26, American Chemical Society, Dec. 21, 1992, pp. 7373-7381.

\* cited by examiner

MOLDED OR EXTRUDED ARTICLES COMPRISING POLYHYDROXYALKANOATE COPOLYMER AND AN ENVIRONMENTALLY DEGRADABLE THERMOPLASTIC POLYMER

FIELD OF INVENTION

The present invention relates to compositions comprising polyhydroxyalkanoate copolymer and an environmentally degradable thermoplastic polymer or copolymer. The compositions are used to make molded or extruded disposable articles, in particular, tampon applicator members that are readily environmentally degradable.

BACKGROUND OF THE INVENTION

This invention relates to the need for developing new plastic materials that can be used in applications where biodegradability, compostability or biocompatibility are among primary desirable features of such applications. There have been many attempts to make degradable articles. However, because of costs, the difficulty in processing, and end-use properties, there has been little commercial success. Many compositions that have excellent degradability have only limited processability. Conversely, compositions which are more easily processable have reduced degradability.

An example of a molded or extruded article that accumulates in the environment is a plastic tampon applicator. Paper tampon applicators are considered environmentally friendly in that they readily disintegrate in a sewage system and/or can be disposed of through aerobic, anaerobic, or natural degradation processes. However, paper tampon articles are not most favored among females due to pledget insertion difficulties associated with their use. Certain female consumers prefer plastic tampon applicators because the plastic applicators are easier to insert, however, most plastic tampon applicators are made from polymeric materials that are not biodegradable and that do not readily soften or break-up into smaller fragments for decomposition in a sewage system, resulting in increased environmental concerns.

An applicator made from water soluble polymers such as polyvinyl alcohol suffers from moisture sensitivity, stability, odor, or stickiness. Further, a plastic tampon applicator constructed from water soluble polymers, such as polyvinyl alcohol and polyethylene oxide, does not provide enough in-use integrity during insertion and tends to stick to sewer pipes after flushing which can lead to clogging of toilet systems and/or drain pipes.

Polyhydroxyalkanoates (PHAs) are thermoplastic polymers desirable for use in molded or extruded articles particularly due to their biodegradability. U.S. Pat. No. 5,498,692, issued Mar. 12, 1996 to Noda, and U.S. Pat. No. 5,502,116, issued Mar. 26, 1996 to Noda, relate to molded articles comprising PHAs. Molded articles from such PHAs remain substantially tacky after they are cooled down from the melt, and remain as such until sufficient crystallinity sets in, particularly with PHA copolymers levels above 10 wt %. Residual tack typically can lead to material sticking to itself or to the processing equipment, or both, and thereby can restrict the speed at which a polymeric product is produced or prevent the product from being collected in a form of suitable quality. A poly(3-hydroxybutyrate-co-3-hydroxyvalerate) product commercialized under the name BIOPOL® suffers from hardness, brittleness, and from having very slow crystallization kinetics. Similarly, U.S. Pat. No. 5,292,860 to Shiotani lacks teachings regarding compositions having short cycle times in the manufacturing process for molded or extruded articles.

Consequently, there is a need for melt processable compositions of environmentally degradable polymers for use in molded or extruded articles where the polymers have economically viable annealing cycle times. Moreover, the compositions should be suitable for use in conventional processing equipment, and resultant molded or extruded articles should meet consumer acceptability for their structural integrity and aesthetic characteristics of smoothness, flexibility, reduced stickiness, stability, and the like.

SUMMARY OF THE INVENTION

Molded or extruded articles of the present invention comprise a blend of a PHA copolymer and an environmentally degradable thermoplastic polymer or copolymer. Such blends demonstrate desired environmental degradability and an annealing cycle time that is at least ten seconds less than an annealing cycle time to form a molded or extruded article lacking the environmentally degradable thermoplastic polymer or copolymer.

In one embodiment, the molded or extruded article comprising a blend of the present invention is a flushable tampon applicator that is greater than 50% disintegrated within 28 days under anaerobic conditions.

Another embodiment of the present invention is an environmentally degradable molded or extruded article comprising at least 5% parts by weight of an environmentally degradable thermoplastic polymer or copolymer; and at least 20% parts by weight of a polyhydroxyalkanoate copolymer comprising at least two randomly repeating monomer units wherein a first monomer unit has structure (I) where $R^1$ is $CH_3$, and n is 1; and wherein a second monomer unit has structure (II) where $R^2$ is C3 alkyl. In this embodiment, the amount of the randomly repeating monomer units having the structure of the second monomer unit is less than 20%.

A further embodiment of the present invention is an environmentally degradable molded or extruded article as set forth in the previous paragraph wherein the PHA copolymer is a first PHA copolymer and the environmentally degradable thermoplastic polymer or copolymer is a second PHA copolymer comprising at least two randomly repeating monomer units (I) and (II) as recited above wherein the percentage of units of structure (II) is other than the percentage of units of structure (II) present in the first PHA copolymer.

A process of forming an environmentally degradable molded or extruded article comprises heating to a molten state such a PHA copolymer and an environmentally degradable thermoplastic polymer or copolymer as described herein to form a blend, allowing the melted blend to anneal, and molding or extruding the article, the process having an annealing cycle time that is at least ten seconds less than an annealing cycle time to form a molded or extruded article lacking the environmentally degradable thermoplastic polymer or copolymer.

Filed on an even date herewith is USSN, of the present inventors to molded or extruded articles comprising PHA copolymer compositions having short annealing cycle times.

DETAILED DESCRIPTION OF THE INVENTION

Polyhydroxyalkanoate Copolymers (PHAs)

The environmentally degradable molded or extruded article comprises at least 5% parts by weight of the environmentally degradable thermoplastic polymer or copolymer; and at least 20% parts by weight of a PHA copolymer comprising at least two randomly repeating monomer units (RRMUs) wherein a first monomer unit has structure (I)

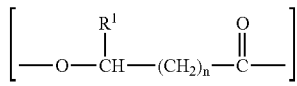

where $R^1$ is H, or C1 or C2 alkyl, and n is 1 or 2; and wherein a second monomer unit has

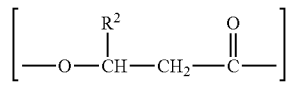

structure (II) where $R^2$ is a C3–C19 alkyl or C3–C19 alkenyl, or the second monomer unit has structure (III)

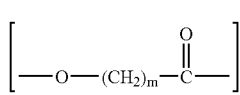

where m is from 2 to 9, and where at least 80% of the randomly repeating monomer units has the structure of the first monomer unit. In one embodiment, R1 is a methyl group ($CH_3$). In a further embodiment of the first RRMU, R1 is methyl and n is 1, whereby the polyhydroxyalkanoate copolymer comprises 3-hydroxybutyrate units. Generally, the length of $R^2$ will, to some extent, influence the reduction in overall crystallinity of the copolymer. In one embodiment, $R^2$ is a C3–C15 alkyl group or alkenyl group. In a further embodiment, $R^2$ is a C3–C9 alkyl group, a C5 or C7 alkyl group, or a C3 alkyl group. The alkyl or alkenyl group may be branched or straight chain. In alternate embodiments, $R^2$ is a C15–C19 alkyl or alkenyl group. Additionally, the length of $(CH_2)_m$ will generally, to some extent, influence the reduction in overall crystallinity of the copolymer. In one embodiment, m is from 2 to 9, from 2 to 4, or m is 3.

To obtain the advantageous combination of physical properties exhibited by the blended molded or extruded articles, at least about 80 mole percent of the copolymer comprise RRMUs having the structure of the first RRMU of formula (I). Suitably, the molar ratio of the first RRMUs to the second RRMU in the copolymer is in the range of from about 80:20 to about 98:2, from about 85:15 to about 96:4, or from about 90:10 to about 94:6. In addition, the PHA copolymer suitably has a number average molecular weight of greater than about 150,000 g/mole, and further has a melting point designated Tm 1.

In further embodiments of the first polyhydroxyalkanoate copolymer employed in the compositions of the molded or extruded articles, one or more additional RRMUs may be included. Suitably, the additional RRMUs may have the structure (IV):

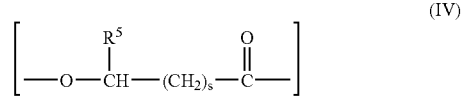

wherein $R^5$ is H, or a C1–C19 alkyl or alkenyl group and s is 1 or 2, with the provision that the additional RRMUs are not the same as the first or second RRMUs.

The C4C6 polyhydroxyalkanoate copolymers set forth herein can be synthesized by chemical or biological methods as disclosed, for example, by Noda in U.S. Pat. No. 5,990,271, Noda, et al. in U.S. Pat. No. 5,942,597, both of which are incorporated herein by reference, Fukui, T. and Doi, Y. *Appl. Microbiol. Biotechnol*, 49:333–336 (1998), and Kichise, T. et al. *Int'l. J. of Biological Macromolecules*, 25:69–77 (1999). The amount of C6 in the final product is determined by standard methods such as NMR or GC MS methods such as described in Doi, Y. et al., *Macromolecules* 28, 4822 (1995) and Fukui, T. et al., *Biomacromolecules* 3, 618 (2002).

Environmentally Degradable Thermoplastic Polymers or Copolymers for Blending with a PHA Copolymer An environmentally degradable thermoplastic polymer or copolymer that is substantially compatible with a PHA copolymer is blended with a PHA copolymer in the present invention. As used herein, the term "substantially compatible" means when heated to a temperature above the softening and/or the melting temperature of the composition, the polymer is capable of forming a substantially homogeneous mixture with the PHA copolymer after molding. The thermoplastic polymer used must be able to flow upon heating and, in certain embodiments, resolidify faster than that of the PHA copolymer, such as, for example, by vitrification.

The degradable polymer used here to blend with a PHA copolymer must have a melting temperature sufficiently low for low processing temperature of the mixture to maintain the thermal stability of the PHA copolymer and yet be sufficiently high for quick solidification of the mixture in processing to ensure the moldability or extrudability during use of the molded or extruded article. Suitable melting temperatures of degradable polymers are from about 50° C. to about 200° C., in another embodiment from about 60° C. to about 180° C., and in a further embodiment about 160° C. or less. Thermoplastic polymers having a melting temperature above 200° C. may be used if plasticizers or diluents are used to lower the observed melting temperature. The polymer must have rheological characteristics suitable for moldability or extrudability.

The molecular weight of the degradable polymer must be sufficiently high to enable entanglement between polymer molecules to provide enough strength for desired physical properties. Environmentally degradable thermoplastic polymers for blends of the present invention have molecular weights above 10,000 g/mol, in another embodiment above 50,000 g/mol, and in a further embodiment above 100,000 g/mol. "Molecular weight" or "average molecular weight" for polymers, unless otherwise indicated, refers to number average molecular weight.

A degradable thermoplastic polymer for blending with a PHA copolymer may be a second environmentally degradable PHA polymer or copolymer, or blend thereof. In one embodiment, the second PHA polymer or copolymer comprises at least two randomly repeating monomer units (I) and (II) as recited above wherein the percentage of units of structure (II) is other than the percentage of units of structure (II) present in the first polyhydroxyalkanoate copolymer. In one embodiment, the percentage of units of structure (II) of the second PHA is less than the percentage of units of structure (II) in the first PHA. In another embodiment, the first PHA copolymer has a percentage of monomer unit structure (II) of 10–18% and the second PHA copolymer has a percentage of monomer unit structure (II) of 2–8%.

In a further embodiment, the second PHA polymer or copolymer comprises at least one randomly repeating monomer unit having the structure (V):

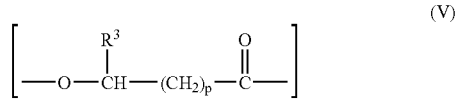

wherein $R^3$ is H, or C1 or C2 alkyl, and p is 1 or 2. In one embodiment, $R^3$ is a methyl group ($CH_3$). In a further embodiment, $R^3$ is methyl and p is 1, whereby the second PHA polymer comprises 3-hydroxybutyrate units. In a further embodiment, the second PHA polymer is the polyhydroxybutyrate homopolymer. Optionally, the second environmentally degradable polymer comprises two or more additional randomly repeating monomer units selected from the group consisting of the structures (VI) and (VII):

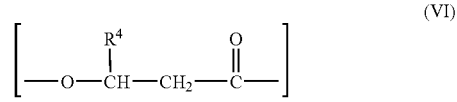

wherein $R^4$ is a C2–C19 alkyl or C2–C19 alkenyl, and

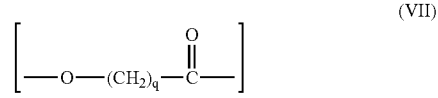

wherein q is from 2 to about 16. With reference to the second RRMU comprising a monomer of structure (VII), q is from 2 to about 10, or from about 4 to about 8. In a further embodiment, q is about 5. When present, the additional randomly repeating monomer units represent no more than 25% of the total monomer units and, in another embodiment less than 15%, wherein the second PHA homo- or copolymer suitably has a number average molecular weight of greater than about 50,000 g/mole. The value of the melting point is generally determined by DSC (Differential Scanning Calorimetry) and is taken as the highest endothermic peak temperature observed on the DSC heating scan using, for example, the method outlined in ASTM D 3418.

Further examples of environmentally degradable thermoplastic polymers suitable for blending with the PHA copolymer for use in the present invention include aliphatic polyesteramides; diacids/diols aliphatic polyesters; modified aromatic polyesters including modified polyethylene terephthalates, modified polybutylene terephthalates; aliphatic/aromatic copolyesters; polycaprolactones; polyesters and polyurethanes derived from aliphatic polyols (i.e., dialkanoyl polymers); polyamides including polyethylene/vinyl alcohol copolymers; polyhydroxycarboxylic acids; lactic acid polymers including lactic acid homopolymers and lactic acid copolymers; lactide polymers including lactide homopolymers and lactide copolymers; glycolide polymers including glycolide homopolymers and glycolide copolymers; and mixtures thereof.

Specific examples of aliphatic polyesteramides suitable for use as an environmentally degradable thermoplastic polymer herein include, but are not limited to, aliphatic polyesteramides which are reaction products of a synthesis reaction of diols, dicarboxylic acids, and aminocarboxylic acids; aliphatic polyesteramides formed from reacting lactic acid with diamines and dicarboxylic acid dichlorides; aliphatic polyesteramides formed from caprolactone and caprolactam; aliphatic polyesteramides formed by reacting acid-terminated aliphatic ester prepolymers with aromatic diisocyanates; aliphatic polyesteramides formed by reacting aliphatic esters with aliphatic amides; and mixtures thereof. Aliphatic polyesteramides formed by reacting aliphatic esters with aliphatic amides are suitable. Also suitable in the present invention are polyvinyl alcohol and its copolymers.

Aliphatic polyesteramides which are copolymers of aliphatic esters and aliphatic amides can be characterized in that these copolymers generally contain from about 30% to about 70%, or from about 40% to about 80% by weight of aliphatic esters, and from about 30% to about 70%, or from about 20% to about 60% by weight of aliphatic amides. The weight average molecular weight of these copolymers range from about 10,000 g/mol to about 300,000 g/mol, or from about 20,000 g/mol to about 150,000 g/mol as measured by the known gel chromatography technique used in the determination of molecular weight of polymers.

The aliphatic ester and aliphatic amide copolymers of suitable aliphatic polyesteramides are derived from monomers such as dialcohols including ethylene glycol, diethylene glycol, 1,4-butanediol, 1,3-propanediol, 1,6-hexanediol, and the like; dicarboxylic acids including oxalic acid, succinic acid, adipic acid, oxalic acid esters, succinic acid esters, adipic acid esters, and the like; hydroxycarboxylic acid and lactones including caprolactone, and the like; aminoalcohols including ethanolamine, propanolamine, and the like; cyclic lactams including s-caprolactam, lauric lactam, and the like; (o-aminocarboxylic acids including aminocaproic acid, and the like; 1:1 salts of dicarboxylic acids and diamines including 1:1 salt mixtures of dicarboxylic acids such as adipic acid, succinic acid, and the like, and diamines such as hexamethylenediamine, diaminobutane, and the like; and mixtures thereof. Hydroxy-terminated or acid-terminated polyesters such as acid terminated oligoesters can also be used as the ester-forming compound. The hydroxyl-terminated or acid terminated polyesters typically have weight or number average molecular weights of from about 200 g/mol to about 10,000 g/mol.

Aliphatic polyesteramides may comprise copolymer combinations of adipic acid, 1,4-butanediol, and 6-aminocaproic acid with an ester portion of 45%; adipic acid, 1,4-butanediol, and s-caprolactam with an ester portion of 50%; adipic acid, 1,4-butanediol, and a 1:1 salt of adipic acid and 1,6-hexamethylenediamine; and an acid-terminated oligoester made from adipic acid, 1,4-butanediol, 1,6-hexamethylenediamine, and s-caprolactam. These aliphatic polyesteramides have melting points of from about 115° C. to about 155° C. and relative viscosities (1 wt. % in m-cresol at 25° C.) of from about 2.0 to about 3.0, and are commercially available from Bayer Aktiengesellschaft (BAK, Leverkusen, Germany). A specific example of a commercially available polyesteramide is BAK 404-004.

Specific examples of diacids/diols aliphatic polyesters suitable for use as an environmentally degradable thermoplastic polymer herein include, but are not limited to, aliphatic polyesters produced either from ring opening reactions or from the condensation polymerization of acids and alcohols, wherein the number average molecular weight of these aliphatic polyesters typically range from about 30,000 g/mol to about 50,000 g/mol. Suitable diacids/diols aliphatic polyesters are reaction products of a C2–C10 diol reacted with oxalic acid, succinic acid, adipic acid, suberic acid, sebacic acid, copolymers thereof, or mixtures thereof. Nonlimiting examples of diacids/diols include polyalkylene succinates such as polyethylene succinate, and polybutylene succinate; polyalkylene succinate copolymers such as polyethylene succinate/adipate copolymer, and polybutylene succinate/adipate copolymer; polypentamethyl succinates; polyhexamethyl succinates; polyheptamethyl succinates; polyoctamethyl succinates; polyalkylene oxalates such as polyethylene oxalate, and polybutylene oxalate; polyalkylene oxalate copolymers such as polybutylene oxalate/succinate copolymer and polybutylene oxalate/adipate copolymer; polybutylene oxalate/succinate/adipate terpolyers; and mixtures thereof. An example of a suitable commercially available diacid/diol aliphatic polyester is the polybutylene succinate/adipate copolymers sold as BIONOLLE® 1000 series and BIONOLLE® 3000 series from the Showa Highpolymer Company, Ltd. (Tokyo, Japan).

Specific examples of aliphatic/aromatic copolyesters suitable for use as an environmentally degradable thermoplastic polymer herein include, but are not limited to, those aliphatic/aromatic copolyesters that are random copolymers formed from a condensation reaction of dicarboxylic acids or derivatives thereof and diols. Suitable dicarboxylic acids include, but are not limited to, malonic, succinic, glutaric, adipic, pimelic, azelaic, sebacic, fumaric, 2,2 dimethyl glutaric, suberic, 1,3-cyclopentanedicarboxylic, 1,4-cyclohexanedicarboxylic, 1,3-cyclohexanedicarboxylic, diglycolic, itaconic, maleic, 2,5-norbornanedicarboxylic, 1,4-terephthalic, 1,3-terephthalic, 2,6-naphthoic, 1,5-naphthoic, ester forming derivatives thereof, and combinations thereof. Suitable diols include, but are not limited to, ethylene glycol, diethylene glycol, triethylene glycol, tetraethylene glycol, propylene glycol, 1,3-propanediol, 2,2-dimethyl-1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, and combinations thereof. Nonlimiting examples of such aliphatic/aromatic copolyesters include a 50/50 blend of poly(tetramethylene glutarate-co-terephthalate), a 60/40 blend of poly(tetramethylene glutarate-co-terephthalate), a 70/30 blend of poly(tetramethylene glutarate-co-terephthalate), an 85/15 blend of poly(tetramethylene glutarate-co-terephthalate), a 50/45/5 blend of poly(tetramethylene glutarate-co-terephthalate-co-diglycolate), a 70/30 blend of poly(ethylene glutarate-co-terephthalate), an 85/15 blend of poly(tetramethylene adipate-co-terephthalate), an 85/15 blend of poly(tetramethylene succinate-co-terephthalate), a 50/50 blend of poly(tetramethylene-co-ethylene glutarate-co-terephthalate), and a 70/30 blend of poly(tetramethylene-co-ethylene glutarate-co-terephthalate). These aliphatic/aromatic copolyesters, in addition to other suitable aliphatic/aromatic polyesters, are further described in U.S. Pat. No. 5,292,783 issued to Buchanan et al. on Mar. 8, 1994, which descriptions are incorporated by reference herein. An example of a suitable commercially available aliphatic/aromatic copolyester is the poly(tetramethylene adipate-co-terephthalate) sold as EASTAR BIO® Copolyester from Eastman Chemical or ECOFLEX® from BASF.

Specific examples of lactic acid polymers and lactide polymers suitable for use as an environmentally degradable thermoplastic polymer herein include, but are not limited to, those polylactic acid-based polymers and polylactide-based polymers that are generally referred to in the industry as "PLA". Therefore, the terms "polylactic acid", "polylactide" and "PLA" are used interchangeably to include homopolymers and copolymers of lactic acid and lactide based on polymer characterization of the polymers being formed from a specific monomer or the polymers being comprised of the smallest repeating monomer units. In other words, polylatide is a dimeric ester of lactic acid and can be formed to contain small repeating monomer units of lactic acid (actually residues of lactic acid) or be manufactured by polymerization of a lactide monomer, resulting in polylatide being referred to both as a lactic acid residue containing polymer and as a lactide residue containing polymer. It should be understood, however, that the terms "polylactic acid", "polylactide", and "PLA" are not intended to be limiting with respect to the manner in which the polymer is formed.

Suitable lactic acid and lactide polymers include those homopolymers and copolymers of lactic acid and/or lactide which have a weight average molecular weight generally ranging from about 10,000 g/mol to about 600,000 g/mol, from about 30,000 g/mol to about 400,000 g/mol, or from about 50,000 g/mol to about 200,000 g/mol. An example of commercially available polylactic acid polymers include a variety of polylactic acids that are available from the Chronopol Incorporation located in Golden, Colo., and the polylactides sold under the tradename EcoPLA®. Examples of suitable commercially available polylactic acid is NATUREWORKS® from Cargill Dow and LACEA® from Mitsui Chemical. Particularly suitable is a homopolymer or copolymer of polylactic acid having a melting temperature from about 160° to about 175° C. Modified polylactic acid and different stereo configurations may also be used, such as poly L-lactic acid and poly D,L-lactic acid with D-isomer levels up to 75%. In particular, the PLA is semi-crystalline where at least about 90 or 95 mole percent of the repeating units in the polylactide is either L- or D-lactide.

The environmentally degradable thermoplastic polymer or copolymer may be destructured starch. Since natural starch generally has a granular structure, it needs to be destructured before it can be melt processed. Commonly, starch is destructured by dissolving the starch in water. The term "thermoplastic starch" means starch destructured with a plasticizer.

Suitable naturally occurring starches can include, but are not limited to, corn starch, potato starch, sweet potato starch, wheat starch, sago palm starch, tapioca starch, rice starch, soybean starch, arrow root starch, bracken starch, lotus starch, cassava starch, waxy maize starch, high amylose corn starch, and commercial amylose powder. Blends of starch may also be used. Though all starches are useful herein, the present invention is most commonly practiced with natural starches derived from agricultural sources, which offer the advantages of being abundant in supply, easily replenishable and inexpensive in price such as corn starch, wheat starch, and waxy maize starch.

Modified starch is destructured starch and may also be used. Modified starch is defined as non-substituted or substituted starch that has had its native molecular weight characteristics changed (i.e. the molecular weight is changed but no other changes are necessarily made to the starch). If modified starch is desired, chemical modifications of starch typically include acid or alkali hydrolysis, or oxidative chain scission to reduce molecular weight or molecular weight distribution. Natural, unmodified starch generally has a very high average molecular weight and a broad molecular weight distribution (e.g. natural corn starch has an average molecular weight of up to about 60,000,000 grams/mole (g/mol)). The average molecular weight of starch can be reduced to the desirable range for the present invention by acid reduction, oxidation reduction, enzymatic reduction, hydrolysis (acid or alkaline catalyzed), physical/mechanical degradation (e.g., via the thermomechanical energy input of the processing equipment), or combinations thereof. The thermomechanical method and the oxidation method offer an additional advantage when carried out in situ. The exact chemical nature of the starch and molecular weight reduction method is not critical as long as the average molecular weight is in an acceptable range. Ranges of molecular weight for starch or starch blends added to the melt is from about 3,000 g/mol to about 10,000,000 g/mol, from about 10,000 g/mol to about 2,000,000 g/mol, or from about 20,000 g/mol to about 1,000,000 g/mol.

For gelatinization, the starch can be destructurized in the presence of a solvent which acts as a plasticizer. The solvent and starch mixture is heated, typically under pressurized conditions and shear to accelerate the gelatinization process. Chemical or enzymatic agents may also be used to destructure the starch by oxidation or derivatization, for example.

Although not required, substituted starch, also a destructured starch, can be used. If substituted starch is desired, chemical modifications of starch typically include etherification or esterification. Substituted starches may be desired for better compatibility or miscibility with the PHA copolymer. However, this must be balanced with the reduction in their rate of degradability. The degree of substitution of the chemically substituted starch is from about 0.01 to 3.0 or, in a further embodiment, from about 0.01 to 0.06.

The weight of starch in the composition includes starch and its naturally occurring bound water content. The term "bound water" means the water found naturally occurring in starch and before mixing of starch with other components to make the composition of the present invention. The term "free water" means the water that is added in making the composition of the present invention. A person of ordinary skill in the art would recognize in light of the present disclosure that once the components are mixed in a composition, water can no longer be distinguished by its origin. The starch typically has a bound water content of about 5% to 16% by weight of starch. It is known that additional free water may be incorporated as the polar solvent or plasticizer, and not included in the weight of the starch.

Exemplary starches that may be used in the present invention are StarDri 100, STADEX® 10, STADEX® 15, or STADEX® 65, all from Staley. STADEX® 10 and STADEX® 15 are white dextrin from dent corn starch. These dextrins have low solubility in cold water and are used as binders in adhesive applications where high viscosity is required. STADEX® 65 is also a white dextrin from dent corn starch, has medium solubility in cold water and is used as a binder in adhesive applications where high viscosity at medium solids level is required. The StarDri materials are pre-destructured multidextrin starches typically used in food applications.

Typically, the polyhydroxyalkanoate copolymer is present in a blend in an amount of at least 20% parts by weight, or 30%, 40%, 50%, 60%, 70%, 80% or 90% parts by weight of the molded or extruded article. The environmentally degradable thermoplastic polymer or copolymer is present in a blend in an amount of at least 2% parts by weight, or 5%, 10%, 20%, 30%, 40%, 50%, 60%, 70%, or 80%, parts by weight of the molded or extruded article. For anaerobically degradable articles, the total polyhydroxyalkanoate copolymer content is greater than 50%, greater than 60%, or greater than 70% since the degradation rate of environmentally degradable polymers other than polyhydroxyalkanoates may be slower in the absence of oxygen.

Optional Ingredients

Optional materials may be used as processing aids to modify the processability and/or to modify physical properties such as elasticity, tensile strength and modulus of the final product. Other benefits include, but are not limited to, stability including oxidative stability, brightness, color, flexibility, resiliency, workability, processing aids, viscosity modifiers, and odor control. These optional ingredients may be present in quantities of less than about 70%, from about 0.1% to about 50%, or from about 0.1% to about 40% by weight of the composition.

Plasticizers may be used in the composition to modify the mechanical properties of products formed from the composition. In general, a plasticizer tends to lower the modulus and tensile strength, and to increase the ultimate tensile elongation, impact strength, and tear strength of the polymeric product. The plasticizer may also be used to lower the melting point of the composition to thereby enable melt-processing at lower temperatures and to minimize energy requirements and thermal degradation. These plasticizers are typically not required in order to obtain the advantageous combination of properties discussed above.

Nonlimiting examples of plasticizers include hydroxyl plasticizers, sugar alcohols, polyols, hydrogen bond forming organic compounds which do not have hydroxyl group, including urea and urea derivatives, anhydrides of sugar alcohols, animal proteins, vegetable proteins, organic acid esters which are biodegradable, aliphatic acids, or the like. Suitable plasticizers are exemplified by glycerol triacetate, methyl ricinolate, dimethyl sebacate, dihexyl phthalate, caprolactone diol, caprolactone triol, and others such as those described in the above referenced U.S. Pat. Nos. 3,182,036 and 5,231,148.

In further embodiments, a plasticizer is selected from the group consisting of dimethyl sebacate, glycerin, triacetin, glycerol, monostearate, sorbitol, erythritol, glucidol, mannitol, sucrose, ethylene glycol, propylene glycol, diethylene glycol, triethylene glycol, diethylene glycol dibenzoate, dipropylene glycol dibenzoate, triethylene glycol caprate-caprylate, butylene glycol, pentamethylene glycol, hexamethylene glycol, diisobutyl adipate, oleic amide, erucic amide, palmitic amide, dimethyl acetamide, dimethyl sulfoxide, methyl pyrrolidone, tetramethylene sulfone, oxa monoacids, oxa diacids, polyoxa diacids, diglycolic acids, triethyl citrate, acetyl triethyl citrate, tri-n-butyl citrate, acetyl tri-n-butyl citrate, acetyl tri-n-hexyl citrate, alkyl lactates, phthalate polyesters, adipate polyesters, glutate polyesters, diisononyl phthalate, diisodecyl phthalate, dihexyl phthalate, alkyl alylether diester adipate, dibutoxyethoxyethyl adipate, and mixtures thereof. Suitable molecular weights are less than about 20,000 g/mol, less than about 5,000 g/mol, or less than about 1,000 g/mol. If present, the amount of plasticizer in the final molded or extruded article composition is from about 0.1% to about 70%, from about 0.5% to about 50% or from about 1% to about 30%.

Nucleating agents are generally used to increase the crystallization rate, reduce the size of crystals, and improve transparency. Nucleating agents can also improve the melt-flow and demolding behavior of partly crystalline plastic materials such as thermoplastic polyesters. A second polyhydroxyalkanoate such as polyhydroxybutyrate can act as a nucleating agent for the first polyhydroxyalkanoate and thereby improve the crystallization rate of the first polyhydroxyalkanoate such as disclosed by Autran, et al. WO02/055581 and WO02/50156, each filed Dec. 20, 2001. Further nucleating agents include talc, boron nitride, titanium oxide, micromica, chalk, salts, sorbitol acetal, clay, calcium carbonate, sodium chloride, calcium phosphate, LICOMONT® CaV 102 and LICOMONT® NaV 101 (the calcium and sodium salt, respectively, of montanic acid, i.e., long chain (C28–C32) linear carboxylic acids) both of which are commercially available from the Clariant Corporation (Coventry, R.I.); and MILLAD® 3988 (1,2,3,4-bis-(3,4-dimethylbenzylidene sorbitol) which is commercially available from Milliken Chemical (Inman, S.C.). Nucleating agents commonly constitute from about 0.01% to about 5% of the weight of the molded or extruded articles, when used.

Further optional ingredients include salts, slip agents, crystallization accelerators or retarders, odor masking agents, cross-linking agents, emulsifiers, surfactants, cyclodextrins, lubricants, other processing aids, optical brighteners, antioxidants, flame retardants, dyes, pigments, fillers, proteins and their alkali salts, waxes, tackifying resins, extenders, chitin, chitosan, and mixtures thereof.

A filler may further be selected from the group of clays, silica, mica, wollastonite, calcium hydroxide, calcium carbonate, sodium carbonate, magnesium carbonate, barium sulfate, magnesium sulfate, kaolin, calcium oxide, magnesium oxide, aluminum hydroxide, talc, titanium dioxide, wood flour, walnut shell flour, alpha cellulose floc, cellulose fibers, chitin, chitosan powders, organosilicone powders, nylon powders, polyester powders, polypropylene powders, starches, and mixtures thereof. When used, the amount of filler is from 0.1% to 60% by weight of the molded or extruded article.

A lubricant may, for example, be selected from the group consisting of metal soaps, hydrocarbon waxes, fatty acids, long-chain alcohols, fatty acid esters, fatty acid amides, silicones, fluorochemicals, acrylics, and mixtures thereof. When used, the amount of lubricant is from 0.1% to 20% by weight of the molded or extruded article.

Natural polymers may also be used in the present invention. Suitable protein-based polymers include soy protein, zein protein, and combinations thereof. The natural polymer may be present in an amount of from about 0.1% to about 80% or from about 1% to about 60%.

Extrusion and Molding

As used herein, a "molded or extruded article" is an object that is formed from a PHA copolymer blended with an environmentally degradable thermoplastic polymer and formed using molding or extrusion techniques such as injection molding, blow molding, compression molding or extrusion of pipes, tubes, profiles, cables, or films. Molded or extruded articles may be solid objects such as, for example, toys, or hollow objects such as, for example, bottles, containers, tampon applicators, applicators for insertion of medications into bodily orifices, medical equipment for single use, surgical equipment, or the like.

Injection molding of thermoplastics is a multi-step process by which a composition of the present invention is heated until it is molten, then forced into a closed mold where it is shaped, and finally solidified by cooling. The PHA copolymer blends are melt processed at melting temperatures less than about 180° C. or, more typically, less than about 160° C. to minimize thermal degradation.

Three common types of machines that are used in injection molding are ram, screw plasticator with injection, and reciprocating screw devices (see *Encyclopedia of Polymer Science and Engineering*, Vol. 8, pp. 102–138, John Wiley and Sons, New York, 1987 ("EPSE-3"). A ram injection molding machine is composed of a cylinder, spreader, and plunger. The plunger forces the melt in the mold. A screw plasticator with a second stage injection consists of a plasticator, directional valve, a cylinder without a spreader, and a ram. After plastication by the screw, the ram forces the melt into the mold. A reciprocating screw injection machine is composed of a barrel and a screw. The screw rotates to melt and mix the material and then moves forward to force the melt into the mold.

An example of a suitable injection molding machine is the Engel Tiebarless ES 60 TL apparatus having a mold, a nozzle, and a barrel that is divided into zones wherein each zone is equipped with thermocouples and temperature-control units. The zones of the injection molding machine can be described as front, center, and rear zones whereby the pellets are introduced into the front zone under controlled temperature. The temperature of the nozzle, mold, and barrel components of the injection molding machine can vary according to the melt processing temperature of the pellets and the molds used, but will typically be in the following ranges: nozzle, 120–170° C.; front zone, 100–160° C.; center zone, 100–160° C.; rear zone, 60–150° C.; and mold, 5–50° C. Other typical processing conditions include an injection pressure of from about 2100 kPa to about 13,790 kPa, a holding pressure of about 2800 kPa to about 11,032 kPa, a hold time of about 2 seconds to about 15 seconds, and an injection speed of from about 2 cm/sec. to about 20 cm/sec. Examples of other suitable injection molding machines include Van Dorn Model 150-RS-8F, Battenfeld Model 1600, and Engel Model ES80.

Compression molding in thermoplastics consists of charging a quantity of a composition of the present invention in the lower half of an open die. The top and bottom halves of the die are brought together under pressure, and then the molten composition conforms to the shape of the die. The mold is then cooled to harden the plastic (see EPSE-3).

Blow molding is used for producing bottles and other hollow objects (see EPSE-3). In this process, a tube of molten composition known as a parison is extruded into a closed, hollow mold. The parison is then expanded by a gas, thrusting the composition against the walls of a mold. Subsequent cooling hardens the plastic. The mold is then opened and the article removed.

Blow molding has a number of advantages over injection molding. The pressures used are much lower than injection molding. Blow molding can be typically accomplished at pressures of about 170 kPa to about 690 kPa between the plastic and the mold surface. By comparison, injection molding pressures can reach about 69,000 kPa to about 137,900 kPa (see EPSE-3). In cases where the composition has a molecular weight too high for easy flow through molds, blow molding is the technique of choice. High molecular weight polymers (or copolymers) often have better properties than low molecular weight polymers, for example high molecular weight materials have greater resistance to environmental stress cracking. (see EPSE-3). It is possible to make extremely thin walls in products with blow molding. This means less composition is used, and solidification times are shorter, resulting in lower costs through material conservation and higher throughput. Another important feature of blow molding is that since it uses only a female mold, slight changes in extrusion conditions at the parison nozzle can vary wall thickness (see EPSE-3). This is an advantage with structures whose necessary wall thicknesses cannot be predicted in advance. Evaluation of articles of several thicknesses can be undertaken, and the thinnest, thus lightest and cheapest, article that meets specifications can be used.

Extrusion is used to form extruded articles, such as pipes, tubes, rods, cables, or profile shapes. Compositions are fed into a heating chamber and moved through the chamber by a continuously revolving screw. Single screw or twin screw extruders are commonly used for plastic extrusion. The composition is plasticated and conveyed through a pipe die head. A haul-off draws the pipe through the calibration and cooling section with a calibration die, a vacuum tank calibration unit and a cooling unit. Rigid pipes are cut to length while flexible pipes are wound. Profile extrusion may be carried out in a one step process. Extrusion procedures are further described in Hensen, F., *Plastic Extrusion Technology*, p 43–100.

Flushable tampon applicators of the present invention are molded or extruded in a desired shape or configuration using a variety of molding or extrusion techniques to provide a thermoplastic applicator comprising an outer tubular member and an inner tubular member or plunger. In another embodiment, the outer tubular member and plunger may be made by different molding or extrusion techniques, and in a further embodiment, the outer member is molded or extruded from a blend of the present invention and the plunger is made from another environmentally degradable material.

Generally, the process of making flushable tampon applicators of the present invention involves charging a composition of the present invention into a compounder, and the composition is melt blended and processed to pellets. The pellets are then constructed into flushable tampon applicators using an injection molding apparatus. The injection molding process is typically carried out under controlled temperature, time, and speed and involves melt processing pellets or thermoplastic compositions wherein the melted thermoplastic composition is injected into a mold, cooled, and molded into a desired plastic object. Alternatively, the composition can be charged directly into an injection molding apparatus and the melt molded into the desired flushable tampon applicator.

One example of a procedure of making flushable tampon applicators of the present invention involves extruding the blend at a temperature above the melting temperature of the composition to form a rod, chopping the rod into pellets, and injection molding the pellets into the desired flushable tampon applicator form.

The compounders that are commonly used to melt blend thermoplastic compositions are generally single-screw extruders, twin-screw extruders, and kneader extruders. Examples of commercially available extruders suitable for use herein include the Black-Clawson single-screw extruders, the Werner and Pfleiderer co-rotating twin-screw extruders, the HAAKE® Polylab System counter-rotating twin screw extruders, and the Buss kneader extruders. General discussions of polymer blending and compounding are disclosed in the *Encyclopedia of Polymer Science and Engineering*; Volume 6, pp. 571–631, 1986, and Volume 11, pp. 262–285, 1988; John Wiley and Sons, New York; which disclosures are incorporated by reference herein.

The flushable tampon applicators of the present invention can be packaged in any suitable wrapper provided that the wrapper is soil proof and disposable with dry waste. Suitable wrappers are those made from biodegradable materials which create minimal or no environmental concerns for their disposal. It is contemplated, however, that the tampon applicators of the present invention can be packaged in flushable wrappers made from paper, nonwoven, cellulose, thermoplastic, or any other suitable flushable material, or combinations of these materials.

Annealing Cycle Time

The annealing cycle time is defined herein as holding time plus cooling time. With process conditions substantially optimized for a particular mold, an annealing cycle time is a function of copolymer blend composition. Process conditions substantially optimized are the temperature settings of the zones, nozzle, and mold of the molding apparatus, the shot size, the injection pressure, and the hold pressure. Annealing cycle times provided herein for a PHA copolymer blended with an environmentally degradable polymer are at least ten seconds shorter than such times for a PHA copolymer absent the blend. In further embodiments of the invention, annealing cycle times provided herein are at least 15, 20, 25, 30, 35, 40, 45, or 50 seconds less than an annealing cycle time to form an environmentally degradable molded or extruded article lacking the environmentally degradable thermoplastic polymer or copolymer. A dogbone tensile bar having dimensions of ½ inch length (L) (12.7 mm)×⅛ inch width (W) (3.175 mm)×1/16 inch height (H) (1.5875 mm) made using an Engel Tiebarless ES 60 TL injection molding machine as provided herein provides a standard as representative of a molded or extruded article for measuring annealing cycle times herein.

The holding time is the length of time that a part is held under a holding pressure after initial material injection. The result is that air bubbles and/or sink marks, preferably both, are not visually observable on the exterior surface, preferably both exterior and interior surfaces (if applicable), with the naked eye (of a person with 20-20 vision and no vision defects) from a distance of about 20 cm from the surface of the molded or extruded article. This is to ensure the accuracy and cosmetic quality of the part. Shrinkage is taken into account by the mold design, however, shrinkage of about 1.5% to 5%, from about 1.0% to 2.5%, or 1.2% to 2.0% may occur. A shorter holding time is determined by reducing the holding time until parts do not pass the visual test described supra, do not conform to the shape and texture of the mold, are not completely filled, or exhibit excessive shrinkage. The length of time prior to the time at which such events occur is then recorded as a shorter holding time.

The cooling time is defined as the time for the part to become solidified in the mold and to be ejected readily from the mold. The mold includes at least two parts, so that the molded article is readily removed. For removal, the mold is opened at the parting line of the two parts. The finished molded part can be removed manually from the opened mold, or it can be pushed out automatically without human intervention by an ejector system as the mold is being opened. Depending on the part geometry, such ejectors may consist of pins or rings, embedded in the mold, that can be pushed forward when the mold is open. For example, the mold can contain standard dial-type or mechanical rod-type ejector pins to mechanically assist in the ejection of the molded parts. Suitable size rod-type ejector pins are ⅛ inch (3.175 mm), and the like. A shorter cooling time is determined by reducing the cooling time until parts become hung up on the mold and cannot readily pop out. The length of time prior to the time at which the part becomes hung up is then recorded as a shorter cooling time.

Processing temperatures that are set low enough to avoid thermal degradation of the polymer blend material, yet high enough to allow free flow of the material for molding are used. The PHA copolymer blends are melt processed at melting temperatures less than about 180° C. or, more typically, less than about 160° C. to minimize thermal degradation. In general, polymers can thermally degrade when exposed to temperatures above the degradation temperature after melt for a period of time. As is understood by those skilled in the art in light of the present disclosure, the particular time required to cause thermal degradation will depend upon the particular material, the length of time above the melt temperature (Tm), and the number of degrees above the Tm. The temperatures can be as low as reasonably possible to allow free-flow of the polymer melt in order to minimize risk of thermal degradation. During extrusion, high shear in the extruder increases the temperature in the extruder higher than the set temperature. Therefore, the set temperatures may be lower than the melt temperature of the material. Low processing temperatures also help to reduce cycle time. For example, without limitation, the set temperature of the nozzle and barrel components of the injection molding machine can vary according to the melt processing temperature of the polymeric materials and the type of molds used and can be from about 20° C. degrees below the Tm to about 30° C. above the Tm, but will typically be in the following ranges: nozzle, 120–170° C.; front zone, 100–160° C.; center zone, 100–160° C.; rear zone, 60–160° C. The set mold temperature of the injection molding machine is also dependent on the type of polymeric materials and the type of molds used. A higher mold temperature helps polymers crystallize faster and reduces the cycle time. However, if the mold temperature is too high, the parts may come out of the mold deformed. The mold temperature is 5–60° C. Typically, the mold temperature is 25–50° C.

Molding injection speed is dependent on the flow rate of the compositions. The higher flow rate, the lower viscosity, the lower speed is needed for the injection molding. Injection speed can range from about 5 cm/sec to 20 cm/sec, in one embodiment, the injection speed is 10 cm/sec. If the viscosity is high, the injection speed is increased so that extruder pressure pushes the melt materials into the mold to fill the mold. The injection molding pressure is dependent on the processing temperature and shot size. Free flow is dependent upon the injection pressure reading not higher than about 14 Mpa.

Environmental Degradability and Flushability

The molded or extruded articles produced in the present invention are environmentally degradable. "Environmentally degradable" is defined as being biodegradable, disintegratable, dispersible, or compostable or a combination thereof. "Flushable" as used herein means that an article can be safely flushed into a sewer system without detrimental consequences to existing sewage infrastructure systems. As a result, molded or extruded articles of the present invention can be easily and safely disposed of in solid waste composting or wastewater collection and treatment systems. The environmental degradability of the molded or extruded articles of the present invention offers a solution to the problem of accumulation of such materials in the environment following their use. The flushability of the molded or extruded articles of the present invention when used in disposable products, such as tampon applicators, offer additional convenience and discreteness to the consumer. Although biodegradability, disintegratability, dispersibility, compostibility, and flushability all have different criteria and are measured through different tests, generally the molded or extruded articles of the present invention will meet more than one of these criteria.

Biodegradable is defined as when an organic material is exposed to aerobic conditions, the material will break down into simple compounds such as carbon dioxide and water or, under anaerobic conditions, the material will break down into simple compounds such as carbon dioxide, water, and methane by the action of natural occurring microorganisms. Biodegradability means that the organic constituents of the molded or extruded articles are subject to decomposition via biological activity and there is an absence of persistent metabolites.

A variety of different standardized biodegradability methods have been established by various organizations and in different countries. For example, for aerobic biodegradability, the American Society for Testing and Materials (ASTM) has established ASTM D 5338 (Standard Test Method for the Determining Aerobic Biodegradation of Plastic Materials Under Controlled Composting Conditions) for municipal solid waste composting, and ASTM D 5271 (Standard Test Method for Assessing the Aerobic Biodegradation of Plastic Materials in an Activated Sludge Wastewater Treatment System) for municipal wastewater treatment. These tests measure the percent of test material that mineralizes as a function of time by monitoring the amount of carbon dioxide being released as a result of assimilation by microorganisms in the matrix of interest. The carbon dioxide production in these tests is typically measured via electrolytic respirometry. Other standard protocols, such 301B from the Organization for Economic Cooperation and Development (OECD), may also be used to assess the aerobic biodegradability of a material. Standard biodegradation tests in the absence of oxygen are described in various protocols such as ASTM D 5511 (Standard Test Method for Determining the Anaerobic Biodegradation of Plastic Materials Under High Solids Anaerobic Digestion Conditions) or ASTM D 5526 (Standard Test Method for Determining Anaerobic Biodegradation of Plastic Materials Under Accelerated Landfill Conditions). These tests are used to assess the biodegradability of materials in septic tanks, anaerobic digestion or sanitary landfills.

Disintegration is when the molded or extruded article has the ability to break up into smaller pieces by physical, chemical, or biological means. Disintegration is assessed by determining the weight loss of a material under specific environmental conditions. Both aerobic and anaerobic disintegration tests are used. In these tests the weight loss is typically determined by the amount of test material that is no longer retained on an 18 mesh sieve with 1 millimeter openings after exposure to activated or digester sludge. The difference in weight between the initial sample and the sample recovered on a screen is used to determine the rate and extent of disintegration. The testing for biodegradability and disintegration are similar since essentially the same environment is used for testing. The major difference is that the weight of the material remaining is measured for disintegration, while the evolved gases are measured for biodegradability.

Molded or extruded articles of the present invention have greater than 50% disintegration within 28 days under anaerobic conditions and, in further embodiments, greater than 60%, or greater than 80% disintegration in 28 days under such conditions.

EXAMPLES

Molded Test Samples Comprising PHA copolymer; and PHA Copolymer Blended with an Environmentally Degradable Polymer or Copolymer The following compositions are compounded and molded into test samples. The various compositions have designations as follows:

| COMPOSITION | COMPONENTS OF COMPOSITION IN WEIGHT PERCENT |
|---|---|
| 1. | PHA[1] |
| 2. | PHA[1]/PHB[2]/DMSA[3]/TiO2[4]/KemamideE[5] = 77/3/17/2/1 |
| 3. | PHA[1]/PHB[2]/DMSA[3]/TiO2[4]/KemamideE[5]/BIONOLLE® 3001[6] = 64/3/15/2/1/15 |
| 4. | PHA[1]/PHB[2]/DMSA[3]/TiO2[4]/KemamideE[5]/PLA[7] = 55/2/10/2/1/30 |
| 5. | PHA[1]/PHB[2]/DMSA[3]/TiO2[4]/KemamideE[5]/LDPE[8] = 55/2/10/2/1/30 |
| 6. | PHA[1]/PHB[2]/DMSA[3]/TiO2[4]/KemamideE[5]/EMA[9] = 55/2/10/2/1/30 |
| 7. | PHA[1]/PHB[2]/DMSA[3]/TiO2[4]/KemamideE[5]/EVA[10] = 55/2/10/2/1/30 |
| 8. | LDPE[8] |
| 9. | PHA[1]/PHB[2]/DMSA[3]/TiO2[4]/KemamideE[5]/PHA[13] = 25/3/17/2/1/52 |
| 10. | PHA[1]/PHB[2]/DMSA[3]/TiO2[4]/KemamideE[5]/PHA[12] = 57.75/3/17/2/1/19.25 |
| 11. | PHA[1]/PHB[2]/DMSA[3]/TiO2[4]/KemamideE[5]/PHA[12] = 38.5/3/17/2/1/38.5 |

[1] A polyhydroxyalkanoate copolymer where the units are C4C6 where C4 is —O—CH(CH3)—CH2—C(O)— and C6 is —O—CH(C3H7)—CH2—C(O)— and the amount of C6 is 10–12% of total weight (11.3% C6)
[2] Polyhydroxybutyrate, particle size of 30 μm, available from Goodfellow Cambridge Limited England
[3] Dimethyl sebacate available from Scientific Polymer Products
[4] Titanium dioxide available from DuPont White Pigment & Mineral Products
[5] Euracamide available as Kemamide E Ultra from Crompton Corporation
[6] Diacid-diol aliphatic polyester is available as BIONOLLE® 3001 from the Showa Highpolymer Company, Ltd
[7] Polylactic acid available as BIOMER® L9000 from Biomer, Frost-Kasten-Str., Krailling, Germany
[8] Linear low density PE available as KN226 from Chevron Philips Chemicals
[9] Poly(ethylene-co-methacrylate), where methacrylate content is 27%, is available as TC221 from Exxon-Mobil
[10] Poly(ethylene-co-vinyl acetate), where vinyl acetate content is 28%, is available as ELVAX® VAX260 from DuPont
[12] A polyhydroxyalkanoate copolymer where the units are C4C6 where C4 is —O—CH(CH3)—CH2—C(O)— and C6 is —O—CH(C3H7)—CH2—C(O)— and the amount of C6 is 5–6% of total weight (5.7%/5.9% C6 50/50)
[13] A polyhydroxyalkanoate copolymer where the units are C4C6 where C4 is —O—CH(CH3)—CH2—C(O)— and C6 is —O—CH(C3H7)—CH2—C(O)— and the amount of C6 is 2–3% of total weight (2.5% C6)

Compounding (Polymer Blending). Ingredients are weighed, dry blended together on a weight percent basis, and fed into a Werner Pfleider ZSK-30 co-rotating twin screw extruder having a screw diameter of 30 mm, six heating zones, and a four hole die plate. The melt blend mixture is extruded to the end of the extruder to the die to form four rods. The rods are carried on a conveyor, air cooled, and pelletized using a pelletizer for injection molding.

Alternatively, compositions 9. and 12. are fed into a HAAKE® Polylab System counter-rotating twin screw extruder. The extruder is equipped with a single hole die plate for compounding the dry blended mixture into a single strand of molten plastic that is air-cooled and then pelletized using a pelletizer for injection molding.

Composition 10. is made of 25% of Composition 12. and PHA [1]/PHB[2]/DMSA[3]/TiO2[4]/KemamideE[5]=57.75/2.25/12.75/1.5/0.75 using Werner Pfleider ZSK-30 extruder.

Composition 11. is made of 50% Composition 12. and PHA [1]/PHB[2]/DMSA[3]/TiO2[4]/KemamideE[5]=38.5/1.5/8.5/1/0.5 using Werner Pfleider ZSK-30 extruder.

Injection Molding. An Engel Tiebarless ES 200 TL injection molding machine or an ES 60 TL injection molding machine is used to make tampon applicators or standardized tensile bars termed "dogbones," respectively, using the compounded blends. The injection molding process uses a 25 mm screw and controlled processing conditions of temperature, time, speed, and pressure wherein the pellets are melt processed, injected into a mold, cooled, and then molded into the desired tampon applicator or dogbone tensile bar.

A common injection molding procedure and parameters affecting molding are as follows. The injection molding machine is started and the temperatures are set for the hydraulic oil (for the machine, normally ~30C), for the materials (for four heating zones, see Tables 2, 3, and 4), and for the mold (35C–60C). The screw speed is set for the extruder.

The composition is fed into the hopper of the injection extruder. The screw takes the melt materials directly from the feed hopper and conveys it to the screw tip. The conveying action of the screw builds up pressure in front of its tip. This pressure pushes back the screw. As soon as there is enough supply of melt in the space for one shot, the rotation of the screw stops. At that time the nozzle has been pushed against the sprue bushing of the mold and the mold is clamped, then a sudden controlled pressure surge in the hydraulic cylinder pushes the screw forward and pumps the melt into the mold cavity. This portion of the procedure represents the initial fill cycle where the mold is about 95% volumetric filled and the hydraulic pressure of the injection machine is reached to a maximum.

Manually set parameters include injection speed (high enough to push the materials into the mold and not too high to give a lot of flashings, normally, 10 cm/sec, the range is 5 cm/sec–20 cm/sec), and shot size (too low will not fill the parts, but too high will have a lot of flushings), injection or filling cycle is affected by injection speed, temperature of the hydraulic oil, melt materials and mold, and viscosity of the materials, pressure dependency of screw drive is affected by the viscosity, molecular degradation, crystallinity, and molecular orientation in part surface, the part, and the surface quality.

The holding cycle begins when the hydraulic pressure is changed to the holding pressure. The rest of the materials (~5% volume) is packed into the mold cavity. The mold is held under pressure until the gates (melt materials go through the gates to the molded parts) in the mold freeze off (i.e., no more melt can get in or out of the parts). The time for this cycle is the holding time. Then the hydraulic pressure drops to zero.

Setting parameters include holding pressure (too high creates a lot of flushings, too low will not be able to push the remaining 5% materials into the parts to avoid voids and sink marks), holding time (long enough until the gates freeze off so that no more materials get in and out of the parts to insure the parts quality, otherwise, the parts will have irregular dimensions, voids, or sink marks), and the holding cycle is affected by the switch over to holding pressure, control of pressure reserve effects, temperature of cavity wall, deformation of mold, stability of clamping unit, and magnitude of clamping force effects.

When the molded parts are sufficiently solidified and cooled, the clamping unit opens. The molded parts are in the mold half that is mounted on the movable platen. Ejectors eject the parts at an adjustable distance from the stationary platen. Cooling time is long enough for auto ejection to occur.

Physical Properties. The tensile strength at break, percent elongation at break, and Young's modulus of the present materials are determined according to methods known in the art, for example, ASTM D882-95a test method described in "Standard Test Method for Tensile Properties of Thin Plastic Sheeting", pages 159–167. Compositions as set forth herein are injection molded to form "dogbone-shaped" test samples having dimensions of ½ inch length (L) (12.7 mm)×⅛ inch width (W) (3.175 mm)×1/16 inch height (H) (1.5875 mm). Such test samples are evaluated for tensile strength at break, percent elongation at break, and elastic modulus using an Instron Tensile Tester (Model 1122 from Instron Corporation located in Canton, Mass.) equipped with a 50 pound (22.679692 kg) load cell, grip separation of 2.54 cm, a gage length of 12.7 mm, 5 mm jaw gap, and a crosshead speed of 5.08 cm/minute. For each analysis, the "dogbone-shaped" test sample is stretched until breakage occurs, and a load-versus-extension plot is generated for determining the tensile strength at break, percent elongation at break, and elastic modulus properties. The tensile strength at break is the load at break divided by the cross-sectional area of the test sample, and is defined in units of mega-Pascal or MPa (newton/square meter). The percent elongation at break is determined by dividing the length of the extension at the point of rupture by the gage length, and then multiplying by 100. Young's modulus is the slope of the initial linear portion of the load-extension curve, and is defined in units of MPa.

Hardness properties are determined according to ASTM D2240-97 test method described in "Standard Test Method for Rubber Property-Durometer Hardness, pages 388–391. Compositions as set forth herein are injection molded into "dogbone-shaped" test samples that are stacked in groups of three dogbones per stack wherein each dogbone stack has a total thickness of 3/16 inches (4.7625 mm). The hardness value is measured at various points of the dogbone stack using a hardness instrument such as Model 307 L Shore D Durometer from PTC Instruments, and a mean hardness measurement is determined.

Table 1 provides physical properties of molded test samples of compositions 1.–11.

TABLE 1

Physical Properties of Molded Test Samples (DogBone)

| Composition | Hardness (Shore D) | Break Stress, Mpa | Break Elongation, % | Young's Modulus, Mpa |
|---|---|---|---|---|
| 1. | 47 | 13 | 185 | 192 |
| 2. | 42 | 11 | 700 | 85 |
| 3. | 43 | 13 | 780 | 95 |
| 4. | 57 | 17 | 43 | 200 |
| 5. | 40 | 5 | 12 | 110 |
| 6. | 30 | 3 | 35 | 51 |
| 7. | 33 | 5 | 38 | 62 |
| 8. | 50 | 12 | 130 | 103 |
| 9. | 48 | 17 | 840 | 100 |
| 10. | 46 | 15 | 750 | 90 |
| 11. | 49 | 15 | 760 | 100 |

Composition 1. displays properties of "stickiness" and does not release readily from a mold. Compositions 2.–11. display physical properties that are acceptable for a variety of molded articles and Table 1 teaches one of skill in the art how to choose a particular composition for a particular use. For example, for a softer article, a composition having a lower hardness number and a lower Young's Modulus would be chosen. A larger break elongation indicates a more elastic composition with less brittleness. A higher break stress indicates a stronger integrity and higher durability.

Table 2 provides conditions for compounding using a twin screw extruder for compositions 2–.7. and 9–.11.

TABLE 2

Conditions for Compounding

| Composition | Zone1 (° C.) | Zone2 (° C.) | Zone3 (° C.) | Zone4 (° C.) | Zone5 (° C.) | Zone6 (° C.) | Die (° C.) | Melt (° C.) | Screw Speed (rpm) |
|---|---|---|---|---|---|---|---|---|---|
| 2. | off | off | 120 | 135 | 140 | 145 | 130 | 135 | 100 |
| 3. | off | off | 120 | 130 | 135 | 140 | 125 | 129 | 125 |
| 4. | off | off | 120 | 135 | 140 | 145 | 130 | 137 | 150 |
| 5. | off | off | 120 | 135 | 140 | 145 | 130 | 137 | 150 |
| 6. | off | off | 120 | 135 | 140 | 145 | 130 | 133 | 125 |
| 7. | off | off | 120 | 135 | 140 | 145 | 130 | 133 | 150 |
| 9. | 120 | 140 | 160 | 140 | — | — | — | 155 | 25 |
| 10. | off | off | 120 | 130 | 150 | 140 | 125 | 141 | 125 |
| 11. | off | off | 120 | 130 | 150 | 140 | 125 | 145 | 125 |

The annealing cycle time is defined herein as holding time plus cooling time for forming a molded article under optimized processing conditions of temperature, shot size, injection pressure and hold pressure.

Table 3. provides conditions for injection molding and annealing cycle times for tampon applicators for compositions 2–.6. and 9–.11. For times over 30 seconds, 5 second intervals are used. Under 30 seconds, 1 second intervals are used.

TABLE 3

Injection Molding Conditions and Annealing Cycle Times for Tampon Applicators

| Injection Molding Settings | 2. | 3. | 4. | 5. | 6. | 9. | 10. | 11. |
|---|---|---|---|---|---|---|---|---|
| Zone 1 (° C.) | 127 | 66 | 127 | 127 | 127 | 127 | 127 | 127 |
| Zone 2 (° C.) | 127 | 107 | 127 | 127 | 127 | 127 | 127 | 127 |
| Zone 3 (° C.) | 132 | 127 | 149 | 132 | 132 | 132 | 132 | 132 |
| Nozzle (° C.) | 135 | 132 | 163 | 135 | 135 | 135 | 135 | 135 |
| Mold (° C.) | 35 | 40 | 35 | 35 | 35 | 35 | 35 | 35 |
| Shot Size (cm) | 3.18 | 4.32 | 3.05 | 3.18 | 3.18 | 3.00 | 3.00 | 3.05 |
| Injection Pressure (MPa) | 12.7 | 14.5 | 12.9 | 12.7 | 13.2 | 12.0 | 12.9 | 12.0 |
| Hold Pressure (MPa) | 6.9 | 6.9 | 6.9 | 6.9 | 6.9 | 3.4 | 3.4 | 3.4 |
| Hold Time (sec) | 20 | 15 | 10 | 5 | 20 | 5 | 5 | 5 |
| Cool Time (sec) | 120 | 75 | 120 | 120 | 100 | 20 | 30 | 20 |
| Annealing Cycle Time (sec) | 140 | 90 | 130 | 125 | 120 | 25 | 35 | 25 |

Data of Table 3 demonstrate that the annealing cycle time for a tampon applicator comprising a polyhydroxyalkanoate copolymer having C4C6 units where the amount of C6 is 10–12 mol % is less when blended with another polymer such as a diacid-diol aliphatic polyester (composition 3., 50 seconds less), polylactic acid (composition 4., 10 seconds less), linear low density polyethylene (composition 5., 15 seconds less), or poly(ethylene-co-methacrylate) (composition 6., 20 seconds less). In particular, the annealing cycle time is less when blended with a polyhydroxyalkanoate copolymer having C4C6 units and the amount of C6 is 2–8 mol % (compositions 9. and 11., 115 seconds less; composition 10., 105 seconds less).

Table 4 provides conditions for injection molding and annealing cycle times for standardized molded samples (dogbone) for compositions 2–.4. and 9–.11. The mold designs of applicator and dogbone are different in that a dogbone mold is a conventional runner system with a sprue connected to runners and send materials to four gates. Each gate is opened to a different shaped molding for parts that are used for material physical testing. Dogbone tensile bars are made when only dogbone molding gate is opened and the other three gates are closed. Dogbone tensile bars represent a standardized molded article.

TABLE 4

Injection Molding Conditions and Annealing Cycle Times for Standardized Molded Samples (Dog Bone)

| Injection Molding Settings | 2. | 3. | 4. | 9. | 10. | 11. |
|---|---|---|---|---|---|---|
| Zone 1 (° C.) | 127 | 110 | 127 | 127 | 127 | 127 |
| Zone 2 (° C.) | 127 | 110 | 127 | 127 | 127 | 127 |
| Zone 3 (° C.) | 132 | 116 | 132 | 132 | 132 | 132 |
| Nozzle (° C.) | 135 | 121 | 135 | 135 | 135 | 135 |
| Mold (° C.) Fixed half | 35 | 16 | 35 | 35 | 35 | 35 |
| Movable half | 35 | 38 | 35 | 35 | 35 | 35 |
| Shot Size (cm) | 1.91 | 1.91 | 2.41 | 1.91 | 1.91 | 1.91 |
| Injection Pressure (Mpa) | 5.2 | 5.9 | 11.5 | 4.2 | 4.5 | 4.3 |
| Hold Pressure (Mpa) | 3.4 | 3.4 | 3.4 | 3.4 | 3.4 | 3.4 |
| Hold Time (sec) | 5 | 5 | 5 | 5 | 5 | 5 |
| Cool Time (sec) | 50 | 40 | 20 | 5 | 8 | 14 |
| Annealing Cycle Time (sec) | 55 | 45 | 25 | 10 | 13 | 19 |

Data of Table 4 demonstrate that the annealing cycle time for a standardized test molded article comprising a polyhydroxyalkanoate copolymer having C4C6 units where the amount of C6 is 10–12 mol % is less when blended with another polymer such as a diacid-diol aliphatic polyester (composition 3., 10 seconds less), or polylactic acid (composition 4., 30 seconds less), for example. In particular, the cycle time is less when blended with a polyhydroxyalkanoate copolymer having C4C6 units and the amount of C6 is 2–8 mol % (composition 9., 45 seconds less; composition 10., 42 seconds less; composition 11., 36 seconds less).

Anaerobic Disintegration. The purpose of this test is to assess the biological disintegration of a flushable product under anaerobic conditions. A high rate of disintegration provides evidence that the product will not be recognizable in septic tank septage or anaerobic digester sludge. The product is weighed and added to a 2 L amber glass bottle that contains 1.5 L of anaerobic digester sludge. The bottles are capped with a one-hole stopper to allow for venting of the evolved gases. At the screening level three replicate bottles are placed in an incubator at 35° C. for each product in the test. For confirmatory testing triplicate bottles are prepared for each time point. The test is conducted under static conditions. Periodically (7 day, 14 day and 28 day) a bottle is sacrificed and the content passed through a 1 mm sieve. The material retained on the 1 mm sieve is dried and weighed, and the percent of product weight loss is determined. Table 5 provides such data for molded applicators of compositions 2.–6. and 9.–1.

TABLE 5

Weight Loss in Anaerobic Disintegration Test

| Composition | 7 day (%) | 14 day (%) | 28 day (%) |
|---|---|---|---|
| 2. | 16 | 58 | 91 |
| 3. | 8 | 17 | 62 |
| 4. | 5 | 7 | 8 |
| 5. | 15 | 32 | 41 |
| 6. | 10 | 30 | 44 |
| 9. | 15 | 51 | 93 |
| 10. | 13 | 44 | 96 |
| 11. | 14 | 49 | 90 |

Compositions comprising a polyhydroxyalkanoate copolymer having C4C6 units where the amount of C6 is 10–12 mol % blended with a polyhydroxyalkanoate copolymer having C4C6 units and the amount of C6 is 2–8 mol % provide, in particular, desirable anaerobic disintegration results.

Aerobic Disintegration. The purpose of this test is to assess the fate of a flushable product during onsite aerobic and municipal activated sludge wastewater treatment. A high rate of disintegration would indicate that biological degradation of the material is occurring. This test method is similar to other continuous flow activated sludge tests that have been developed for down-the-drain chemicals. This test differs from other tests in that the endpoint is loss of material mass in the system instead of loss of a specific chemical through the test system. The test apparatus consists of a 6 L glass reactor with a porous stainless steel filter. The stainless steel filter is used to retain the activated sludge solids in the reactor. Raw wastewater is continuously fed to the reactor at a rate of approximately 15 ml/min. This corresponds to a hydraulic retention time (HRT) of about 7 hr. The mixed liquor suspended solids (MLSS) are periodically measured and a portion of the solids wasted on a weekly basis to maintain the MLSS between 2500 to 4500 mg/L. In this test pre-weighed test material is placed in mesh bags (fiberglass screening with a 1.6 mm size opening) and then suspended in the porous pot reactor. At designated time points, one of the mesh bags with test material is removed from the reactor and its content rinsed through a 1 mm sieve. The amount of the material remaining on the 1 mm sieve is then dried and weighed. The loss of test material mass is determined over time.

TABLE 6

Weight Loss of Composition 2. with Different Thicknesses in Aerobic Disintegration Test

| Thickness | 14 Day (%) | 28 Day (%) | 42 Day (%) | 56 Day (%) |
|---|---|---|---|---|
| 5 mil | 100 | 100 | 100 | 100 |
| 17 mil | 17 | 29 | 59 | 75 |
| 60 mil | 8 | 11 | 16 | 26 |

TABLE 7

Tampon Applicator (15–17 mil) Weight Loss in Aerobic Disintegration Test

| Composition | 14 Day (%) | 28 Day (%) | 42 Day (%) | 56 Day (%) |
|---|---|---|---|---|
| 2 | 13 | 24 | 37 | 55 |
| 4 | 3 | 4 | 5 | 6 |
| 5 | 8 | 14 | 19 | 20 |
| 6 | 9 | 11 | 15 | 16 |
| 9 | 17 | 26 | 47 | 51 |
| 10 | 17 | 29 | 42 | 44 |
| 11 | 14 | 24 | 41 | 55 |

Compositions of Table 7 comprising a polyhydroxyalkanoate copolymer having C4C6 units where the amount of C6 is 10–12 mol % blended with a polyhydroxyalkanoate copolymer having C4C6 units and the amount of C6 is 2–8 mol % provide, in particular, desirable aerobic disintegration results. The PHA composition in Table 6 illustrates that the rate of disintegration depends on the thickness of the articles.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An environmentally degradable molded or extruded article comprising:
   at least 5% parts by weight of an environmentally degradable thermoplastic polymer or copolymer; and
   at least 20% parts by weight of a polyhydroxyalkanoate copolymer comprising at least two randomly repeating monomer units
   wherein a first monomer unit has structure (I)

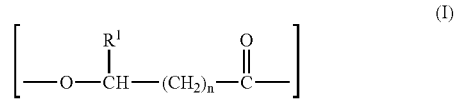

where $R^1$ is H, or C1 or C2 alkyl, and n is 1 or 2; and
wherein a second monomer unit has structure (II)

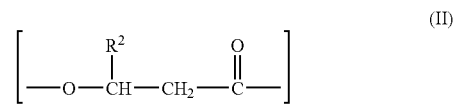

where $R^2$ is a C3–C19 alkyl or C3–C19 alkenyl, or the second monomer unit has structure (III)

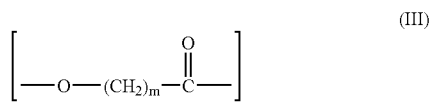

where m is from 2 to 9
wherein at least 80% of the randomly repeating monomer units has the structure of the first monomer unit;
wherein an annealing cycle time to form the molded or extruded article is at least ten seconds less than an annealing cycle time to form a molded or extruded article lacking the environmentally degradable thermoplastic polymer or copolymer.

2. The environmentally degradable molded or extruded article of claim 1 wherein the environmentally degradable thermoplastic polymer or copolymer is a diacid/diol aliphatic polyester, an aliphatic/aromatic copolyester, a polyhydroxycarboxylic acid, starch, or a combination thereof.

3. The environmentally degradable molded or extruded article of claim 1 wherein the environmentally degradable thermoplastic polymer or copolymer is polybutylene succinate/adipate copolymer, polylactide, polycaprolactone, or polyethylene succinate.

4. The environmentally degradable molded or extruded article of claim 1 wherein the polyhydroxyalkanoate copolymer is a first polyhydroxyalkanoate copolymer, and the environmentally degradable thermoplastic polymer or copolymer is a second polyhydroxyalkanoate copolymer having randomly repeating monomer units (I) and (II) and having a percentage of units of structure (II) that is other than the percentage of units of structure (II) present in the first polyhydroxyalkanoate copolymer.

5. The environmentally degradable molded or extruded article of claim 1 wherein $R^1$ is $CH_3$, n is 1 and the second monomer unit has structure II wherein $R^2$ is straight-chain or branched C3 alkyl.

6. The environmentally degradable molded or extruded article of claim 3 wherein the environmentally degradable thermoplastic polymer or copolymer is polylactide polymer or copolymer.

7. The environmentally degradable molded or extruded article of claim 2 wherein the environmentally degradable thermoplastic polymer or copolymer is starch.

8. The environmentally degradable molded or extruded article of claim 1 in the form of a flushable tampon applicator.

9. The environmentally degradable molded or extruded article of claim 1 further comprising a processing aid.

10. The environmentally degradable molded or extruded article of claim 9 wherein the processing aid is a plasticizer selected from the group consisting of dimethyl sebacate, glycerin, triacetin, glycerol, monostearate, sorbitol, erythritol, glucidol, mannitol, sucrose, ethylene glycol, propylene glycol, diethylene glycol, triethylene glycol, diethylene glycol dibenzoate, dipropylene glycol dibenzoate, triethylene glycol caprate-caprylate, butylene glycol, pentamethylene glycol, hexamethylene glycol, diisobutyl adipate, oleic amide, erucic amide, palmitic amide, dimethyl acetamide, dimethyl sulfoxide, methyl pyrrolidone, tetramethylene sulfone, oxa monoacids, oxa diacids, polyoxa diacids, diglycolic acids, triethyl citrate, acetyl triethyl citrate, tri-n-butyl citrate, acetyl tri-n-butyl citrate, acetyl tri-n-hexyl citrate, alkyl lactates, phthalate polyesters, adipate polyesters, glutate polyesters, diisononyl phthalate, diisodecyl phthalate, dihexyl phthalate, alkyl alylether diester adipate, dibutoxyethoxyethyl adipate, and mixtures thereof.

11. The environmentally degradable molded or extruded article of claim 9 wherein the processing aid is a nucleating agent selected from the group of polyhydroxybutyrate, sorbitol acetal, boron nitride, titanium oxide, talc, clay, calcium carbonate, sodium chloride, metal phosphate, and mixtures thereof.

12. The environmentally degradable molded or extruded article of claim 9 wherein the processing aid is a filler selected from the group consisting of clays, silica, mica, wollastonite, calcium hydroxide, calcium carbonate, sodium carbonate, magnesium carbonate, barium sulfate, magnesium sulfate, kaolin, calcium oxide, magnesium oxide, aluminum hydroxide, talc, titanium dioxide, wood flour, walnut shell flour, alpha cellulose floc, cellulose fibers, chitin, chitosan powders, organosilicone powders, nylon powders, polyester powders, polypropylene powders, starches and the mixtures thereof.

13. The environmentally degradable molded or extruded article of claim 9 wherein the processing aid is a lubricant selected from the group consisting of metal soaps, hydrocarbon waxes, fatty acids, long-chain alcohols, fatty acid esters, fatty acid amides, silicones, fluorochemicals, acrylics, and mixtures thereof.

14. An environmentally degradable molded or extruded article comprising:
at least 5% parts by weight of an environmentally degradable thermoplastic polymer or copolymer; and
at least 20% parts by weight of a polyhydroxyalkanoate copolymer comprising at least two randomly repeating monomer units
wherein a first monomer unit has structure (I)

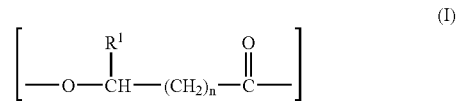

where $R^1$ is $CH_3$, and n is 1; and
wherein a second monomer unit has structure (II)

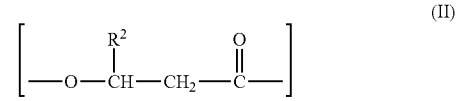

where $R^2$ is C3 alkyl,
wherein up to 20% of the randomly repeating monomer units has the structure of the second monomer unit.

15. The environmentally degradable molded or extruded article of claim 14 wherein an annealing cycle time to form the molded or extruded article is at least ten seconds less than an annealing cycle time to form a molded or extruded article lacking the environmentally degradable thermoplastic polymer or copolymer.

16. The environmentally degradable molded or extruded article of claim 15 wherein the environmentally degradable thermoplastic polymer or copolymer is a diacid/diol aliphatic polyester, an aliphatic/aromatic copolyester, or a polyhydroxycarboxylic acid, starch, or a combination thereof.

17. The environmentally degradable molded or extruded article of claim 15 wherein the article is a tampon applicator and the environmentally degradable thermoplastic polymer or copolymer is polybutylene succinate/adipate copolymer, or polylactide.

18. The environmentally degradable molded or extruded article of claim 15 wherein the polyhydroxyalkanoate copolymer is a first polyhydroxyalkanoate copolymer, and the environmentally degradable thermoplastic polymer or copolymer is a second polyhydroxyalkanoate copolymer having randomly repeating monomer units (I) and (II) and having a percentage of units of structure (II) that is less than the percentage of units of structure (II) present in the first polyhydroxyalkanoate copolymer.

19. The environmentally degradable molded or extruded article of claim 15 wherein the article is a tampon applicator.

20. The environmentally degradable molded or extruded article of claim 15 wherein the annealing cycle time for the molded or extruded article comprising the environmentally degradable thermoplastic polymer or copolymer is at least 15, 20, 25, 30, 35, 40, 45, or 50 seconds less than an annealing cycle time to form an environmentally degradable molded or extruded article lacking the environmentally degradable thermoplastic polymer or copolymer.

21. An environmentally degradable molded or extruded article comprising:
   a first polyhydroxyalkanoate copolymer comprising at least two randomly repeating monomer units
      wherein a first monomer unit has structure (I)

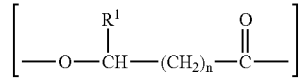
(I)

where R$^1$ is CH$_3$, and n is 1; and
wherein a second monomer unit has structure (II)

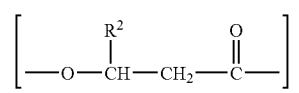
(II)

where R$^2$ is C3 alkyl,
wherein less than 20% of the randomly repeating monomer units has structure (II); and
a second polyhydroxyalkanoate copolymer comprising at least two randomly repeating monomer units (I) and (II) as recited above wherein the percentage of units of structure (II) is other than the percentage of units of structure (II) present in the first polyhydroxyalkanoate copolymer.

22. The environmentally degradable molded or extruded article of claim 21 wherein an annealing cycle time to form the molded or extruded article is at least ten seconds less than an annealing cycle time to form a molded or extruded article lacking the second polyhydroxyalkanoate copolymer.

23. The environmentally degradable molded or extruded article of claim 22 wherein the first polyhydroxyalkanoate copolymer has a percentage of monomer unit structure (II) of 10–18% and wherein the second polyhydroxyalkanoate copolymer has a percentage of monomer unit structure (II) of 2–8%.

24. A flushable tampon applicator comprising:
   at least 5% parts by weight of an environmentally degradable thermoplastic polymer or copolymer; and
   at least 20% parts by weight of a polyhydroxyalkanoate copolymer comprising at least two randomly repeating monomer units
      wherein a first monomer unit has structure (I)

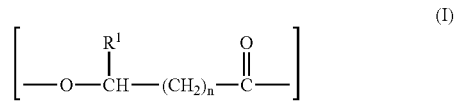
(I)

where R$^1$ is H, or C1 or C2 alkyl, and n is 1 or 2; and
wherein a second monomer unit has structure (II)

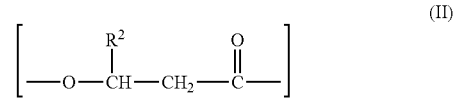
(II)

where R$^2$ is a C3–C19 alkyl or C3–C19 alkenyl,
or the second monomer unit has structure (III)

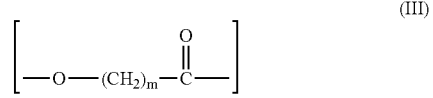
(III)

where m is from 2 to 9
   wherein at least 80% of the randomly repeating monomer units has the structure of the first monomer unit; and
   wherein the applicator is greater than 50% disintegrated within 28 days under anaerobic disintegration conditions.

25. The flushable tampon applicator of claim 24 wherein the applicator is greater than 60% disintegrated within 28 days under anaerobic disintegration conditions.

26. The flushable tampon applicator of claim 24 wherein the applicator is greater than 80% disintegrated within 28 days under anaerobic disintegration conditions.

27. A process of forming an environmentally degradable molded or extruded article, comprising:
   heating to a molten state
      at least 5 % parts by weight of an environmentally degradable thermoplastic polymer or copolymer; and at least 20 % parts by weight of a polyhydroxyalkanoate copolymer comprising
at least two randomly repeating monomer units
wherein a first monomer unit has structure (I)

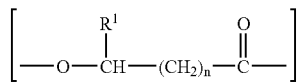
(I)

where $R^1$ is H, or C1 or C2 alkyl, and n is 1 or 2; and
wherein a second monomer unit has structure (II)

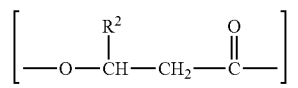
(II)

where $R^2$ is a C3–C19 alkyl or C3–C19 alkenyl, or the second monomer unit has structure (III)

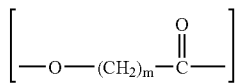
(III)

where m is from 2 to 9
wherein at least 80% of the randomly repeating monomer units has the structure of the first monomer unit to form a blend,
allowing the melted blend to anneal; and
molding or extruding the article, the process having an annealing cycle time that is at least ten seconds less than an annealing cycle time to form a molded or extruded article lacking the environmentally degradable thermoplastic polymer or copolymer.

* * * * *

UNITED STATES PATENT AND TRADEMARK OFFICE
CERTIFICATE OF CORRECTION

PATENT NO. : 7,098,292 B2  Page 1 of 1
APPLICATION NO. : 10/431796
DATED : May 8, 2003
INVENTOR(S) : Jean Jianquin Zhao et al.

It is certified that error appears in the above-identified patent and that said Letters Patent is hereby corrected as shown below:

Column 23, line 10, delete "9.-1."" and insert therefor -- 9.-11. --.

Column 30, line 19, delete "thermosplastic" and insert therefor -- thermoplastic --.

Signed and Sealed this

Twelfth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,098,292 B2  
APPLICATION NO. : 10/431796  
DATED : August 29, 2006  
INVENTOR(S) : Jean Jianquin Zhao et al.

It is certified that error appears in the above-identified patent and that said Letters Patent is hereby corrected as shown below:

Column 23, line 10, delete "9.-1."" and insert therefor -- 9.-11. --.

Column 30, line 19, delete "thermosplastic" and insert therefor -- thermoplastic --.

This certificate supersedes Certificate of Correction issued June 12, 2007.

Signed and Sealed this

Third Day of July, 2007

JON W. DUDAS  
*Director of the United States Patent and Trademark Office*